(12) United States Patent
Maenz et al.

(10) Patent No.: US 6,284,502 B1
(45) Date of Patent: Sep. 4, 2001

(54) PROCESS FOR CONVERTING PHYTATE INTO INORGANIC PHOSPHATE

(75) Inventors: David Daniel Maenz; Henry Leonard Classen; Rex Wayne Newkirk, all of Saskatoon (CA)

(73) Assignee: University of Saskatchewan, Saskatoon ( * ) Notice: Subject to any disclaimer, the term of this patent is extended or adjusted under 35 U.S.C. 154(b) by 0 days.

(21) Appl. No.: 09/377,275

(22) Filed: Aug. 19, 1999

Related U.S. Application Data

(60) Provisional application No. 60/097,485, filed on Aug. 21, 1998.

(51) Int. Cl.[7] ............... A23K 3/00; A61K 33/42; A01N 59/26; C12N 9/00; C12P 3/00
(52) U.S. Cl. ............... 435/168; 424/601; 426/52; 426/54; 435/183; 435/962
(58) Field of Search ................ 424/78.01, 601; 435/183, 168, 962; 426/7, 54, 52

(56) References Cited

U.S. PATENT DOCUMENTS 3,736,147  5/1973  Iacobucci et al. .............. 99/17

FOREIGN PATENT DOCUMENTS

| | | |
|---|---|---|
| 0380343 | 8/1990 | (EP) . |
| 0619369 | 10/1994 | (EP) . |
| 1093408 | 4/1989 | (JP) . |
| WO 93/16175 | 8/1993 | (WO) . |
| WO 95/27406 | 10/1995 | (WO) . |
| WO 95/28850 | 11/1995 | (WO) . |
| WO 98/30681 | 7/1998 | (WO) . |

OTHER PUBLICATIONS

Preparation of a Low–Phytate Feed Mixture and Bioavailability of its Phosphorus to Chicks, Elsevier Science Publishers B.V., Printed 1990, Amsterdam—Printed in The Netherlands.

XP 002062438—Sutardi and Buckle, K.A., "The characteristics of Soybean Phytase", J. of Food Biochem., (1986) 197–216. Food & nutrition Press, Inc., Westport, CN.

*Primary Examiner*—Deborah K. Ware
(74) *Attorney, Agent, or Firm*—Fitch, Even, Tabin & Flannery

(57) ABSTRACT

A process is provided for converting phytate in a food into inorganic phosphate. The process comprises the steps of:

(i) mechanically mixing a slurry comprising:
 (a) 100 parts by weight of the phytate-containing food,
 (b) 60–1000 parts by weight of a solvent mixture which comprises water and a water-immiscible organic solvent having a boiling point of 20–100° C., the water-immiscible organic solvent constituting 20–85% by wt. of the solvent mixture, and
 (c) a phytase; and
(ii) drying the food to remove the organic solvent.

The process has the advantage of enabling a high conversion rate of phytate into inorganic phosphate in an economical manner.

18 Claims, No Drawings

PROCESS FOR CONVERTING PHYTATE INTO INORGANIC PHOSPHATE

CROSS-REFERENCE TO RELATED APPLICATIONS

The present application claims the benefit of U.S. Provisional Application No. 60/097,485, filed Aug. 21, 1998.

BACKGROUND

The present invention is concerned with a process for converting phytate into inorganic phosphate. In particular, it concerns such a process which can be adjuncted to conventional processes which are used to extract oil from oilseeds.

Phytate [myoinositol 1,2,3,4,5,6-hexakis (dihydrogen phosphate)] is found to varying degrees in all plants as the major storage form of phosphorus. Between 60–80% of the total phosphorus in plants is in the form of phytate. Phytate in plants is often found in the form of complexes with cations such as calcium, magnesium or potassium. The resulting complexes are sometimes called phytin. The term phytate as used herein specifically encompasses such phytin complexes. Phytate is poorly digested by monogastric animals. As a result of this, monogastric animals fed a phytate-rich diet may still suffer from illnesses caused by phosphorus deficiency. This is because the phytate phosphorus is not bio-available, and the majority of dietary phytate consumed by a monogastric animal passes through its gastrointestinal tract and is excreted in the faeces. This excretion is a particular concern in areas of intensive livestock production where excessive amounts of phosphorus-enriched manure can be environmentally damaging.

A further problem associated with the presence of phytate in foods is that it forms complexes with multivalent metal cations. This can interfere with the bio-availability of such cations to animals and humans. This can lead to metal deficiency disorders or inadequate bone mineralization, especially in the case of vegetarians, elderly people and infants.

Phytate also has the disadvantage of inhibiting various enzymes in the gastrointestinal tract, including pepsin and trypsin. It is also forms complexes with proteins preventing their digestion. For these reasons, the presence of phytate in a diet is actually anti-nutritional as it reduces the digestibility of co-present proteins.

One solution which has been proposed to solve the above problems is to convert phytate into inorganic phosphate. The phosphorus in inorganic phosphate is bio-available to monogastric animals. This decreases the phosphorus content of faeces, liberates cations previously complexed by the phytate, promotes protein digestion and prevents phytate inhibition of gastrointestinal enzymes. The conversion is known to be effected by treating the phytate either in vitro or in vivo with a phosphatase enzyme called phytase. The reaction products of this conversion are myoinositol and orthophosphate, the latter being termed inorganic phosphate in this specification.

The in vivo conversion is carried out by adding phytase to foods which contain phytate. As a result, both the phytate and phytase are co-present in the gastrointestinal tract where, in theory at least, the phytase can convert the phytate into inorganic phosphate. However, this has proven to be only partially effective resulting at best in the conversion of no more than 55% of the phytate-phosphorus into inorganic phosphate, and usually a significantly smaller proportion. This incomplete conversion is primarily a consequence of the conditions within the gastrointestinal tract being quite different from those which are optimal for phytase activity. The temperature, pH, moisture and mineral content of the digesta are such that phytase is only partially effective in the gastrointestinal tract during the time which it takes for the digesta to pass through it.

The second solution of subjecting phytate-containing foods to in vitro hydrolysis with phytase has been found to be more a effective than the in vivo conversion described above. This is because the conditions of the in vitro reaction can be tailored to those which result in the phytase having its optimum activity. EP-A-0 380 343 describes one example of such a process in which phytate present in soy protein isolates is converted into inorganic phosphate. The conversion is carried out in an aqueous solution using a bacterial phytase at a pH of 2–6 and at a temperature of 20–60° C.

However, it is found that even such treatments are still unsatisfactory. Firstly, the slurry resulting from these treatments has to be dried by driving away the significant amounts of water which are conventionally included. Although such drying is a relatively simple process step, it is nevertheless relatively expensive to carry out due to the bulk of water which has conventionally been used. Such a bulk is necessary firstly to provide the aqueous environment required by the phytase in order for it to be catalytically active, and secondly to facilitate mixing of the slurry which otherwise would form a relatively viscous mass. As a result of this drying problem, such in vitro processes have had limited commercial success. The second problem which has been found is that the conversion of phytate into inorganic phosphate in these in vitro processes is still far from complete unless extremely high concentrations of (relatively expensive) phytase are used. The present inventors have found that this is due to phytate existing in two forms; a phytase-susceptible form and a mineral-bound, phytase-resistant form. The phytase-resistant form has been found to be phytate in the form of a complex with alkaline earth metal cations such as $Mg^{2+}$ and $Ca^{2+}$.

SUMMARY

Accordingly, a first object of the present invention is to provide a commercially viable process for the in vitro conversion of phytate in a food into inorganic phosphate. A second object is to provide such a commercially viable process in which about So malt or more of the phytate is converted into inorganic phosphate. A third object is to adjunct such a process to a conventional process for extracting oil from oilseeds in order to provide, as a by-product, meal enriched with inorganic phosphate suitable for inclusion in an animal feed or for food use generally.

According to a first aspect, the present invention provides a process for converting phytate in a food into inorganic phosphate comprising the steps of (i) mechanically mixing a slurry comprising (a) 100 parts by weight of the phytate-containing food, (b) 60–1000 parts by weight of a solvent mixture which comprises water and a water-immiscible organic solvent having a boiling point of 20–100° C., the water-immiscible organic solvent constituting 20–85% by wt. of the solvent mixture, and (c) a phytase; and (ii) drying the food to remove the organic solvent. Preferably in the above process, the slurry comprises 150–750 parts by weight of the solvent mixture, more preferably 250–600 parts by weight and most preferably 325–475 parts by weight.

DETAILED DESCRIPTION

The above process is capable of converting phytate present in a food into inorganic phosphate at reduced cost compared to previously available in vitro processes and with a high yield. The phytase requires the co-presence of a significant content of solvent in order to effectively catalyse the conversion of phytate into inorganic phosphate. Whilst it has always been assumed in the prior art that this solvent should be exclusively water, the present inventors have surprisingly found that a substantial proportion of this water can be replaced by an immiscible organic solvent without significantly affecting the ability of the phytase to catalyze the conversion of phytate into inorganic phosphate. The use of a solvent system which includes 20–85% by wt., more preferably 40–75% by wt., and most preferably 50–70% by wt. of the water-immiscible organic solvent is able to support phytase activity whilst having the advantage that drying of the slurry subsequently to the phytase-catalyzed conversion to an acceptable moisture content of less than 20 wt. % is substantially cheaper than drying a comparable slurry in which the solvent is formed entirely from water. This is because, the solvent mixture used in the present invention requires the input of less energy to evaporate it from the slurry.

The slurry which is mechanically mixed preferably further comprises a chelating agent for alkaline earth metal cations. Such a chelating agent competes with the phytate for binding inorganic cations, in particular alkaline earth metal cations such as $Ca^{2+}$ and $Mg^{2+}$. This binding of inorganic cations by the chelating agent has the result of converting phytase-resistant phytate into phytase-susceptible phytate which in turn is then capable of being converted into inorganic phosphate by the co-present phytase.

The food which may be processed according to the present invention may be any phytate-containing food. Such foods are those typically derived from plants. According to a particularly preferred aspect of the invention, the food is one which is obtained by mixing crushed oilseeds with an organic solvent to extract the oil from the oilseeds, and then separating the crushed oilseeds adulterated with the solvent from the oil-containing solvent. These are typical steps used to extract oil from, for instance, soybeans, sunflower seeds, rapeseeds, canola seeds, rice, rice bran, maize, cottonseeds, peanuts, safflower seeds, coconuts, palmnuts, walnuts or hazelnuts, or any processed derivative thereof such as defatted soybeans. Other sources of phytate which can be processed include cereal grains such as wheat, barley, triticale, rye, sorghum or oats.

When extracting oil from the above listed seeds, 10–80% by weight (more preferably 35–60% by weight) of crushed oilseeds are mixed with 90–20% by weight (more preferably 65–40% by weight) of the organic solvent, this being typically n-hexane although any other water-immiscible organic solvent can be used which has a boiling point of 20–100° C. After vigorous mixing, oil from the crushed oilseeds migrates into the hexane following which the oil-enriched hexane is separated from the crushed oilseeds on which a residue of the hexane solvent remains. The solvent-adulterated crushed oilseeds typically comprise 15–65% by weight of the solvent and 85–35% by weight of the crushed oilseeds, more preferably 25–50% by weight of the solvent and 75–50% by weight of the crushed oilseeds and most preferably 35–45% by weight of the solvent and 65–55% by weight of the crushed oilseeds. The solvent-adulterated crushed oilseeds are sometimes referred to as marc or white flake in this technical art.

In a typical prior art process for extracting oil from oilseeds, the solvent-adulterated crushed oilseeds would be dried at this stage to remove all traces of the organic solvent. This is not the case in the present invention in which these solvent-adulterated crushed oilseeds are then treated to convert the phytate present into inorganic phosphate. In particular, 100 parts by weight (excluding solvent) of the crushed oilseeds adulterated with the organic solvent are mixed to form a slurry with 10–10,000 Units of phytase per kg of crushed oilseeds, 30–350 parts by weight (more preferably 100–250 parts by weight, most preferably 120–180 parts by weight) of water, and optionally additional water-immiscible organic solvent having a boiling point of 20–100° C., which may be the same or different from the organic solvent used in the oil extraction step, so that the total amount of organic solvent is 30–850 parts by weight (more preferably 125–500 parts by weight, most preferably 200–300 parts by weight). This slurry is subjected to mechanical mixing, for instance using a hobbart mixer, during which the phytase converts phytate present in the crushed oilseeds into inorganic phosphate. The above slurry may further include 0.05–10 parts by weight of the chelating agent. As previously mentioned, this agent competes with the phytate for binding inorganic cations so converting phytase-resistant phytate into phytase-susceptible phytate. The chelating agent is any material which can chelate alkaline earth metal cations. Typical of such chelating agents are bi-, tri-, or tetra-carboxylic acids such as ascorbic acid, phthalic acid, citric acid or EDTA.

More preferably in this step, 100 parts by weight (excluding solvent) of the oilseeds are mixed with 0.5–5 parts by weight of the chelating agent, and 100–1,000 Units of phytase per kg of crushed oilseeds.

The slurry is preferably reacted in the mixer where the phytate is converted into inorganic phosphate by the catalytic action of the phytase for 5 minutes-2 hours, more preferably 15–90 minutes and most preferably 30–75 minutes and at a temperature of preferably 10–70° C., more preferably 20–65° C., and most preferably 40–60° C. The pH of the slurry is preferably 2–8, more preferably 3–6 and most preferably 4.5–5.5. The acidity of the slurry may be due to the presence of the acid chelating agent, although a mineral acid such as HCl or $H_3PO_4$ may alternatively or additionally be included to adjust the slurry's pH to that which is optimum for phytase activity.

Any water-immiscible organic solvent can be used provided that it has a boiling point of 20–100° C. Higher boiling point solvents are tot preferred as they are not easy to evaporate or boil off from the slurry. Naturally, the chosen organic solvent has to have its boiling point above the temperature at which the phytate conversion to inorganic phosphate is carried out. Typical organic solvents having the desired boiling point are aliphatic solvents having at least 5 carbon atoms and preferred solvents are pentane, hexane and heptane, structural isomers thereof, and isooctane.

In a preferred aspect of the invention the slurry further comprises one or more of cereal grains, cereal flour, fat, vitamins, amino acids or one or more enzymes. Cereal grains and cereal flour contain phytate and thin will also advantageously be converted into inorganic phosphate during the treatment with phytase. The presence of one or more enzymes such as a protease, a carboxypeptidase, a cellulase, a xylanase, a mannanase, an amylase, an a-galactosidase, a pectinase, a β-glucanase or an esterase, is also preferable. This is because such enzymes may help to liberate the phytate from plant bodies rendering it more susceptible to the action of the phytase and/or act upon other of the food components in order to improve their digestibility.

In a subsequent step, the food is dried in order to remove at least the organic solvent and preferably at least a part of the aqueous solvent. This can be done by desolventizing the food by for instance heating or spray drying. The resulting dried product preferably has a content of the organic solvent of less than 0.1 wt. %, more preferably less than 0.04 wt. %, and a moisture content of less than 20 wt. %, more preferably less than 15 wt. %.

The resulting inorganic phosphate-enriched food may then be processed into an animal feed or a human food by mixing it with one or more additional alimentary materials as required.

The resulting inorganic phosphate-enriched food is of substantially greater value to humans and all species of production animals compared to the starting food. In particular, the resulting phosphate-enriched feed may be incorporated in the diets of production animals such as chickens, turkeys, pigs, cattle, fish and sheep. Because the resulting feeds have a relatively low or negligible phytate-content, they also have the advantage of improving mineral and protein bio-availability in foods or feeds in which they are incorporated. In particular, cations which become complexed to the chelating agent will be bio-available as the resulting salts are water-soluble. Also bio-availability of proteins in the food is improved as the phytate is no longer available to entrap them in protein-phytate complexes.

The phytase which may be used in the present invention is produced by various microorganisms such as *Aspergillus spp., Rhizopus spp.*, and certain yeasts. Phytase is also produced by various plant seeds, for example wheat, during germination. Preferred phytases include Natuphos® obtainable from BASF Germany, Phytase Novo obtainable from Novo Nordisk and Finase®S obtainable from Alko Ltd.

The amount of phytase required will depend upon the preparation used, the phytate content of the food, and the reaction conditions. The appropriate dosage can easily be estimated by a person skilled in the art. Phytase activity can be determined by using 1% sodium phytate (obtainable from Sigma St. Louis, Mo.) as a substrate. The enzyme reaction is carried out at a pH of 5.5 and at a temperature of 40° C. Phytase releases phosphate groups from phytate. The determination of the released inorganic phosphorus is based on the colour formed by the reduction of a phosphomolybdate complex.

As well as facilitating the drying of the slurry, the copresence of the organic solvent with the water has the advantage of substantially reducing the overall viscosity of the slurry. It has been found that in the absence of the organic solvent, water soluble proteins present in the food can cause the slurry to become so viscous that the necessary mechanical mixing is substantially prevented without the addition of a significant excess of water.

The present invention will now be explained in further detail by way of the following Example. This illustrates how the process of the invention can be incorporated into a typical process used to extract oil from rapeseed. It should be noted that this Example is not intended to restrict the scope of the present invention in any way.

Examples—Rapeseed Processing

Rapeseed contains tiny oil bodies within its cells and is primarily commercially grown in order to yield this oil. Harvested rapeseed was cleaned, dried and pre-conditioned in the known way, The rapeseed was then flaked by rolling to break open the hulls. This was carried out by passing the rapeseed through the nip of a pair of smooth rollers turning at different speeds. The action of these rollers sheared the seeds into flakes whilst rupturing some of the oil cells.

The flakes were then subjected to thermal conditioning at about 80° C. for about 1 hour which broke open the remaining oil cells. This step also helped to improve protein bio-availability in the resulting meal product. The conditioned flakes which contained about 42% by weight oil and about 8% by weight moisture were then fed to a series of low-pressure continuous screw presses where they received a moderate press. This stage extracted about one half of the available rapeseed oil from the rapeseed.

The cake resulting from the screw presses was then conveyed to a Rotocell solvent extractor where the canola oil was extracted with commercial n-hexane. The cake was introduced into the solvent extractor through a vapour-seal unit, where it was deposited into a basket. N-hexane was percolated by gravity through the cake bed so that it diffused into and saturated the cake fragments. The rapeseed oil migrated into the organic solvent and the oil-containing solvent then flowed out through the cake support screen at the bottom of the basket for separation.

The vapour pressure of n-hexane limits the practical operating temperature of the solvent extractor to about 55° C. A higher temperature unduly increases the quantity of solvent vapour which must be recovered. Furthermore, if the cake temperature is at or near the boiling point of the solvent, a vapour phase occurs at the interface between the cake fragments and the solvent which effectively blocks liquid diffusion. In this way, the extractor yielded an essentially liquid phase containing canola oil and n-hexane, and a "solid" phase of oil-extracted rapeseeds adulterated with n-hexane.

In conventional rapeseed processing, the n-hexane adulterated rapeseeds would be desolvented as the next step. However, in accordance with the process of the present invention, the rapeseeds were then subjected to the phytase treatment to convert phytate within the seeds into inorganic phosphate.

1 kg of the crushed oil-extracted rapeseeds containing 0.38 moles of total phosphate in the form of phytate adulterated with 0.3 liters of n-hexane was formed into a slurry with 750 Units of Natuphos®, a phytase obtained from BASF Germany, 1 liter of water and 1.1 liters of additional n-hexane. The amount of phytate present in the oil-extracted rapeseeds may be assayed according to the method of Tangkongchitr et al. described in Cereal Chem., 58, pp 226–228. The resulting slurry was then sealed in a plexiglass vessel maintained at 50° C. by incubation in a water bath and continuously mixed for 1 hour using a dough hook mixing system. At the conclusion of the incubation period, the resulting meal (Sample 1) contained 0.17 moles of inorganic phosphate, equivalent to a conversion of 45°0 C. % by mol. of the starting phytate. Several methods are known for assaying inorganic phosphate such as the method Pons and Guthrie (Ind. Eng. Chem. Anal. Ed. 18, pp 184–186). By way of comparison, an identical treatment was carried out on 1 kg of crushed rapeseeds except that the phytase was omitted. The resulting meal (Sample 2) contained only 0.019 moles of inorganic phosphate equivalent to a conversion rate of only 5% by mol. based on the starting phytate content of the oil-extracted rapeseeds.

A further 1 kg batch of crushed rapeseeds was treated according to Sample 1 above except that citric acid was added to the slurry as a chelating agent to give a final concentration of 0.5% by weight of citric acid in the slurry. The citric acid reduced the pH of the mixture to 5.0. This treatment resulted in a meal (Sample 3) containing 0.32 moles of inorganic phosphate equivalent to a conversion of 85% by mol. of the starting phytate. Sample 3 shows the benefits of combined treatment with both the organic solvent and the chelating agent. Similarly high values of phytate conversion can be achieved by using alternative chelating agents such as EDTA or phthalic acid.

The resulting inorganic phosphate-enriched meals of Samples 1 and 3 were then subjected to desolventizing-toasting. The desolventizing removes the n-hexane for recycling back to the oil extraction step by evaporation from the meal together with a proportion of the water. The resulting dried meal can then be used directly as a high-protein, high-inorganic phosphate supplement for an animal feed or for human food.

What is claimed is:

1. A process for converting phytate in food into inorganic phosphate, the process comprising:
   (i) mechanically mixing about 100 parts by weight of a phytate containing food with a phytase and about 60 to about 1000 parts by weight of a solvent mixture to form a slurry, the solvent mixture comprising:
      (a) about 20% to about 85% by weight of a water immiscible organic solvent having a boiling point of about 20 to about 100° C., and
      (b) water;
   (ii) incubating the slurry for a time and at a temperature effective for allowing conversion of phytate contained in the food into inorganic phosphate; and
   (iii) drying the food to remove organic solvent.

2. A process according to claim 1, wherein the water immiscible organic solvent is about 40% to about 75% by weight of the solvent mixture.

3. A process according to claim 1, wherein the slurry further comprises a chelating agent for alkaline earth metal cations.

4. A process according to claim 1, wherein the phytate containing food for inclusion in the slurry is crushed oilseeds adulterated with organic solvent.

5. A process according to claim 4, wherein the crushed oilseeds adulterated with organic solvent are obtained by a process comprising:
   mixing crushed oilseeds with a water immiscible organic solvent in an amount effective to extract oil from the oilseeds and provide an oil containing solvent; and
   separating the crushed oilseeds from the oil containing solvent to provide crushed oilseeds adulterated with organic solvent.

6. A process according to claim 5, wherein about 10% to about 80% by weight of crushed oilseeds are mixed with about 90% to about 20% by weight of the organic solvent.

7. A process according to claim 5, wherein the solvent adulterated crushed oilseeds comprise about 15% to about 65% by weight solvent and about 85% to about 35% by weight crushed oilseeds.

8. A process according to claim 4, wherein the slurry is formed by mixing:
   about 100 parts by weight of crushed oilseeds adulterated with a solvent;
   about 10 to about 10,000 units of phytase per kg of crushed oilseeds; and
   about 30 to about 350 parts by weight of water.

9. A process according to claim 8, wherein additional organic solvent is added so that the amount of organic solvent in the slurry is about 30 to about 850 parts by weight.

10. A process according to claim 8, wherein the slurry further comprises about 0.05 to about 10 parts by weight of a chelating agent for alkaline earth metal cations.

11. A process according to claim 10, wherein the chelating agent is ascorbic acid, phthalic acid, citric acid or EDTA.

12. A process according to claim 4, wherein the oilseeds are soybeans, sunflower seeds, rapeseeds, canola seeds, rice, rice bran, maze, cottonseeds, peanuts, safflower seeds, coconuts, palmnuts, walnuts or hazelnuts.

13. A process according to claim 8, wherein the mixing step (i) is carried out in a mixer for about 5 minutes to about 2 hours at a temperature of about 10° C. to about 70° C. at a pH of about 2.0 to about 8.0.

14. A process according to claim 8, wherein the organic solvent is pentane, hexane or heptane.

15. A process according to claim 8, wherein the slurry further comprises one or more cereal grains, cereal flour, fats, vitamins, amino acids or one or more enzymes.

16. A process according to claim 15, wherein the one or more enzymes are selected from the group consisting of protease, carboxypeptidase, cellulase, xylanase, mannase, amylase, α-galactosidase, pectinase, β-glucanase, esterase and mixtures thereof.

17. A process for producing an inorganic phosphate enriched food comprising:
   (i) mechanically mixing about 100 parts by weight of a phytate containing food ingredient with a phytase and about 60 to about 1000 parts by weight of a solvent mixture to form a slurry, the solvent mixture comprising:
      (a) about 20% to about 85% by weight of a water immiscible organic solvent having a boiling point of about 20 to about 1000° C., and
      (b) water;
   (ii) incubating the slurry for a time and at a temperature effective for allowing conversion of phytate contained in the food ingredient into inorganic phosphate to provide an inorganic phosphate enriched food ingredient/solvent blend;
   (iii) drying the phosphate enriched food ingredient/solvent blend to remove organic solvent to provide an inorganic phosphate enriched food ingredient; and
   (iv) mixing the inorganic phosphate enriched food ingredient with one or more additional alimentary products to form the inorganic phosphate enriched food.

18. A process for converting phytate in food into inorganic phosphate, the process comprising:
   (i) mechanically mixing about 100 parts by weight of a phytate containing food, a chelating agent, a phytase and about 50 to about 1000 parts by weight of a solvent mixture to form a slurry, the chelating agent in an amount effective for binding inorganic cations in the slurry, the solvent mixture comprising:
      (a) about 20% to about 85% by weight of a water immiscible organic solvent having a boiling point of about 20 to about 100° C., and
      (b) water;
   (ii) incubating the slurry for a time and at a temperature effective for allowing conversion of phytate contained in the food into inorganic phosphate; and
   (iii) drying the food to remove organic solvent.

* * * * *